(12) United States Patent
Shah et al.

(10) Patent No.: US 6,565,562 B1
(45) Date of Patent: May 20, 2003

(54) METHOD FOR THE RADIO FREQUENCY PERFORATION AND THE ENLARGEMENT OF A BODY TISSUE

(75) Inventors: Krishan Shah, Mississauga (CA); Frank Baylis, Beaconsfield (CA)

(73) Assignee: Baylis Medical Company Inc., Montreal (CA)

( * ) Notice: Subject to any disclaimer, the term of this patent is extended or adjusted under 35 U.S.C. 154(b) by 0 days.

(21) Appl. No.: 09/948,700

(22) Filed: Sep. 10, 2001

Related U.S. Application Data

(62) Division of application No. 08/884,470, filed on Jun. 27, 1997, now abandoned.

(51) Int. Cl.[7] .............................................. A61B 18/18
(52) U.S. Cl. ...................... 606/41; 128/898; 606/194; 600/207; 600/585; 604/164.13
(58) Field of Search .............................. 606/32–50, 167, 606/169, 171, 180, 190–200, 213, 1; 604/164.13, 164.1, 264, 96.01–109; 128/898; 600/434, 585, 201, 204, 207

(56) References Cited

U.S. PATENT DOCUMENTS

| | | | | |
|---|---|---|---|---|
| 5,449,369 | A | * | 9/1995 | Imran .......................... 606/159 |
| 6,120,520 | A | * | 9/2000 | Saadat et al. ................ 606/170 |
| 6,251,121 | B1 | * | 6/2001 | Saadat ......................... 606/180 |

FOREIGN PATENT DOCUMENTS

| | | | | |
|---|---|---|---|---|
| WO | 00/18307 | * | 4/2000 | ................... 606/41 |

* cited by examiner

Primary Examiner—Glenn K. Dawson
(74) Attorney, Agent, or Firm—Ogilvy Renault

(57) ABSTRACT

For creating a hole in body tissue and then enlarging the hole, a guidewire has a continuous diameter guidewire body having a proximal end and a distal end, a distal portion including an electrically conductive exposed tip for creating a perforation when RF current is applied and for preventing the creation of a perforation when RF current is not applied. For expanding the hole, a dilator region is provided between the distal end of the guidewire body and the distal portion for expanding the hole, and has a tapered profile. Also for expanding the hole, an inflatable balloon is located circumferentially on the guidewire body, and a catheter located on the guidewire body and in communication with the balloon for delivery of fluid to the balloon for its inflation.

14 Claims, 7 Drawing Sheets

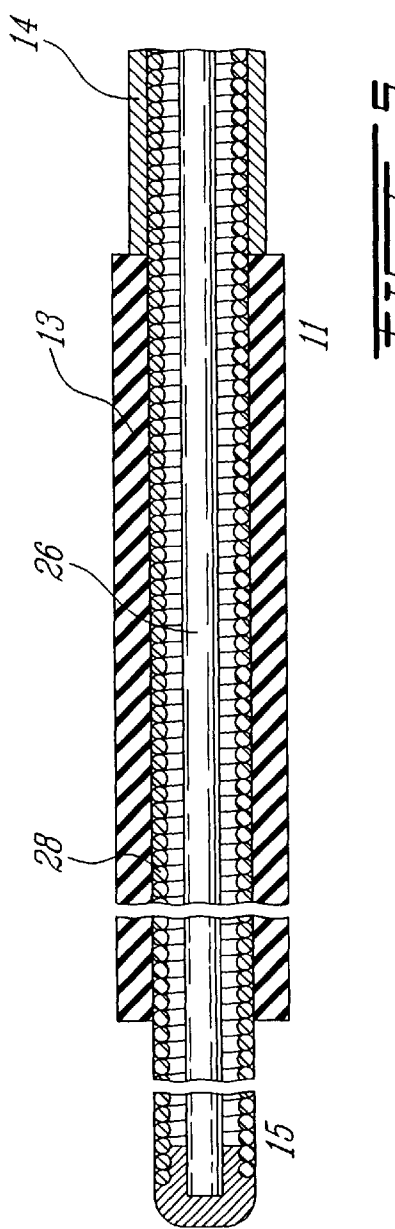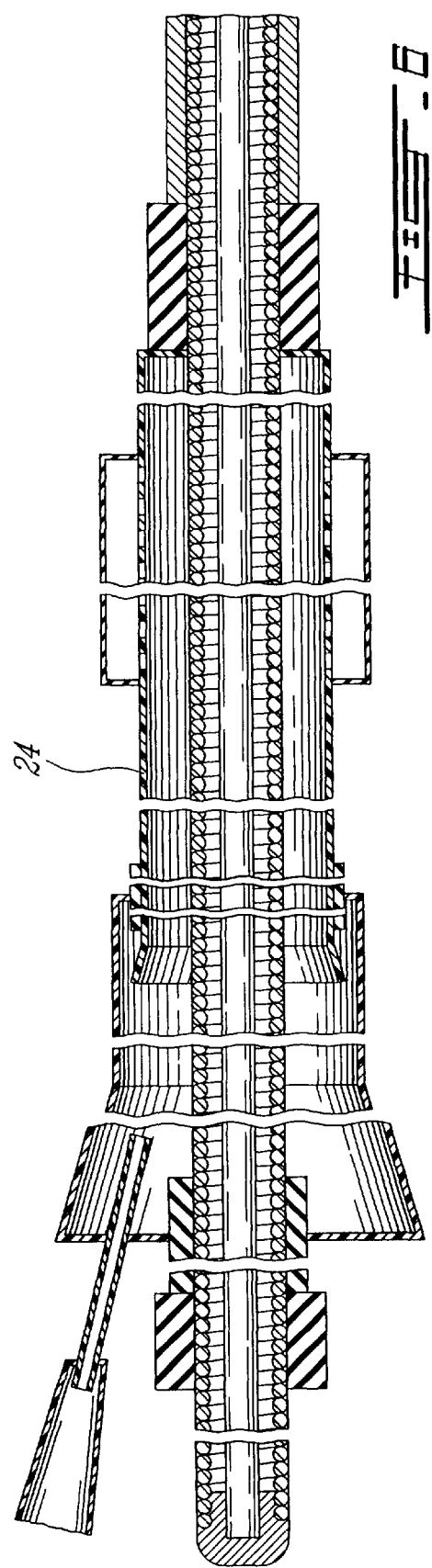

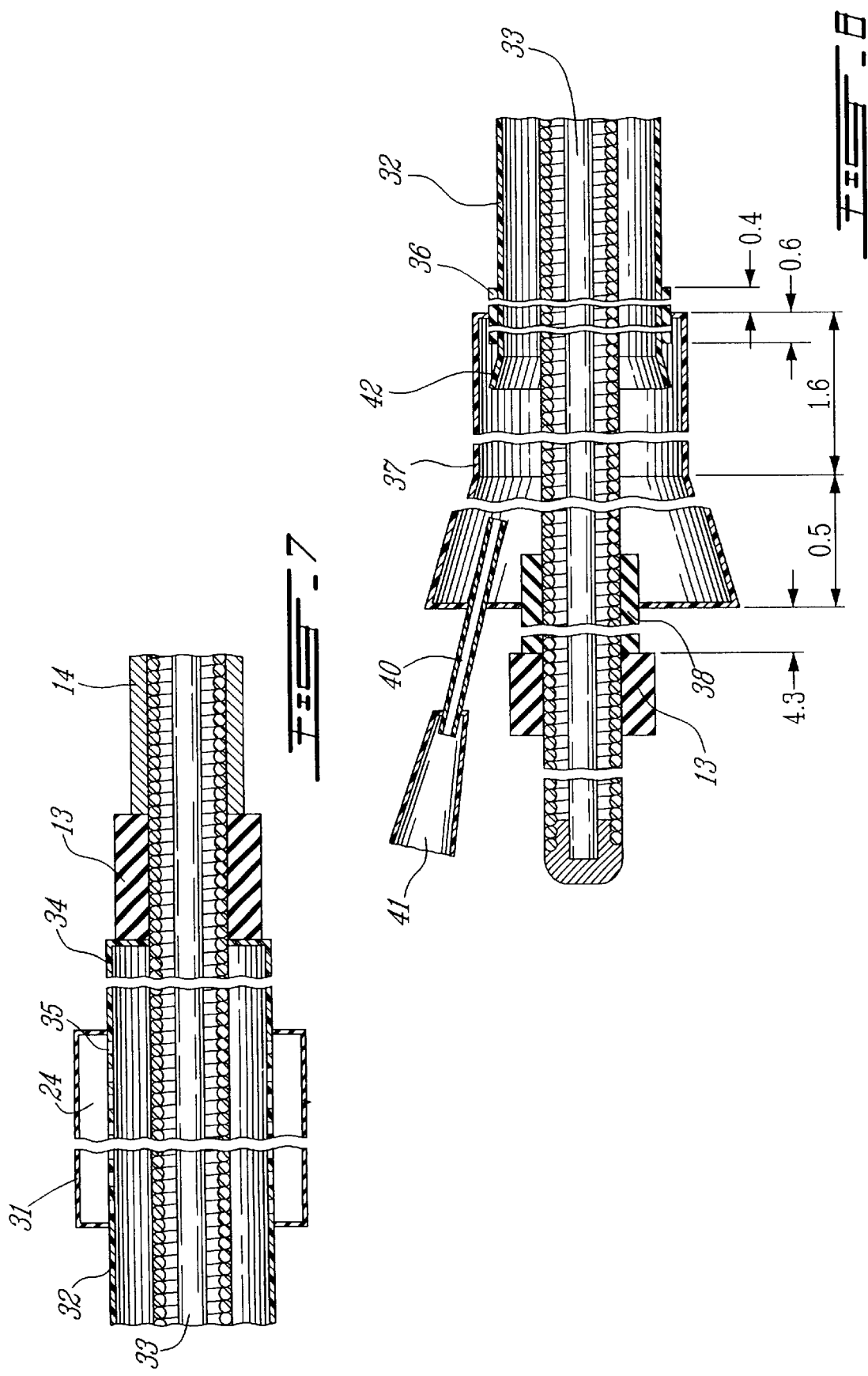

METHOD FOR THE RADIO FREQUENCY PERFORATION AND THE ENLARGEMENT OF A BODY TISSUE

CROSS-REFERENCE TO RELATED APPLICATIONS

This application is a divisional of patent application Ser. No. 08/884,470 filed Jun. 27, 1997 by Applicants, now abandoned.

FIELD OF THE INVENTION

The present invention relates to a radio frequency perforation guidewire as well as a radio frequency generator. The invention is able to allow surgeons and cardiologists to treat pediatric patients that require a transcatheter perforation to deal with congenital heart malfunction. More particularly, the invention is directed to a perforation guidewire which can be energized by radio frequency current to first create, and then enlarge, in a controlled manner, a hole in the atrial septum or any other heart tissue to improve intertribal communication. The invention is applicable to any tissue in the body where it would provide positive results.

BACKGROUND OF THE INVENTION

RF guidewires and catheters for surgical perforation are known in the art. The terms, "guidewire" and "catheter", as used herein, mean substantially the same thing, more explicitly the term catheter means: a tubular medical device for insertion into canals, vessels, passageways, or body cavities, to allow a guidewire passage through, or to deliver or remove fluids, or to permit energy to travel through, or to permit a balloon or any other catheter to be passed over or through it. And the term guidewire means: a wire like medical device that is used to deliver energy to required areas, or used to guide other medical devices, either over or through it.

EP 0 315 730 A3 to Osypka et al. describes a device to dilate and/or open up using heat blood vessels which are morbidly contracted or clogged. U.S. Pat. No. 5,364,393 to Auth et al. describes a guidewire to traverse an occlusion in an arterial lumen to allow subsequent passage of a therapeutic device for treatment.

Newborn pediatric patients who have severe cyanotic problems; patients with pulmonary valve atresia and intact ventricular septum present a formidable therapeutic challenge to pediatric interventional cardiologists. High mortality rates are associated with this congenital heart defect despite numerous advances in the field.

The most common surgical approach consists of creating a systemic to pulmonary artery shunt together with an open pulmonary valvotomy. The final step which is conditional on the right ventricle developing sufficiently is the closure of the atrial septal defect and the systemic to pulmonary shunt.

Alternatively, the feasibility of percutaneous transcatheter "hot tip" laser-assisted balloon dilation has been shown. Several drawbacks exist with the laser system including the necessity of excessive initial capital outlay, risk to staff of retinal damage, and inconvenience of transporting a cumbersome system between laboratories and/or hospitals.

The presence of free electrons and ions in solution within the tissue structure permit the flow of electrical currents. Body tissue has an electrical resistance, and consequently, passage of electrical currents through the body dissipates some energy in the form of heat. At high enough current density levels, vaporization of the entrained tissue water occurs. If the speed of the vaporization process is sufficient to prevent diffusion through tissue, the said tissue will rupture and incise. The aim of electrosurgery is to produce linearly such ruptures.

An electric current can irritate nerve and muscle cells triggering specific reactions such as muscle contractions and sensations of pain. The intensity of the reactions depends on the intensity and frequency of the current used. At frequencies above 100 kilohertz, the muscle fibers are unable to respond.

Electrosurgery is accomplished by passing RF current through a small electrode (the active electrode) in the form of a scalpel or needle into tissue, and completing the electrical circuit through the tissue by attaching a large electrode plate (the indifferent electrode) elsewhere on the body.

OBJECTS AND SUMMARY OF THE INVENTION

It is an object of the present invention to provide an RF perforation guidewire to first create, and then enlarge in a controlled manner, a hole in the atrial septum or any other heart or body tissue to improve intertribal communication.

It is an object of the invention to create new passageways in the tissue.

It is also an object of this invention to traverse through newly created channels in the tissue.

According to one aspect of the invention, there is provided an electrically conductive guidewire for creating a hole in body tissue to be perforated and then enlarging the hole, comprising: a guidewire body with a substantially continuous diameter having a proximal end and a distal end, a distal tip portion including an electrically conductive exposed tip for creating a perforation when RF current is applied and for preventing the creation of a perforation when RF current is not applied, an insulated electrical conductor means for passing electric current from the proximal end to the tip, and a dilator region between the distal end of the guidewire body and the distal tip portion for expanding the hole, and having a tapered profile.

According to another aspect of the invention, there is provided an electrically conductive guidewire for creating a hole in body tissue to be perforated and then enlarging the hole, comprising a guidewire body with a substantially continuous diameter having a proximal end and a distal end, a distal tip portion connected to the distal end of the guidewire body including an electrically conductive exposed tip for creating a perforation when RF current is applied and for preventing the creation of a perforation when RF current is not applied, an insulated electrical conductor means for passing electric current from the proximal end to the tip, an inflatable balloon located circumferentially on the guidewire body for expanding the hole, and a catheter located on the guidewire body and in communication with the balloon for delivery of fluid to the balloon for its inflation.

According to a further aspect of the invention, there is provided an RF signal generator for a surgical RF perforation instrument including an RF voltage source connected to the instrument, an RF impedance measurement circuit for measuring a level of impedance of tissue contacted by the instrument, and control means for monitoring the RF impedance measurement and generating a shut-down control signal when a change in the impedance measured indicates that the instrument has perforated the tissue.

BRIEF DESCRIPTION OF THE DRAWINGS

The invention will be better understood by way of the following detailed description of a preferred embodiment and other embodiments of the invention with reference to the appended drawings, in which:

FIG. 5 is a cross-sectional view of the guidewire with a uniform core;

FIG. 6 is a cross-sectional view of the balloon catheter;

FIG. 7 is a cross-sectional view of the balloon catheter's distal region;

FIG. 8 shows a cross-sectional view of the balloon catheter's proximal region;

DETAILED DESCRIPTION OF THE PREFERRED EMBODIMENT

Figure 1:
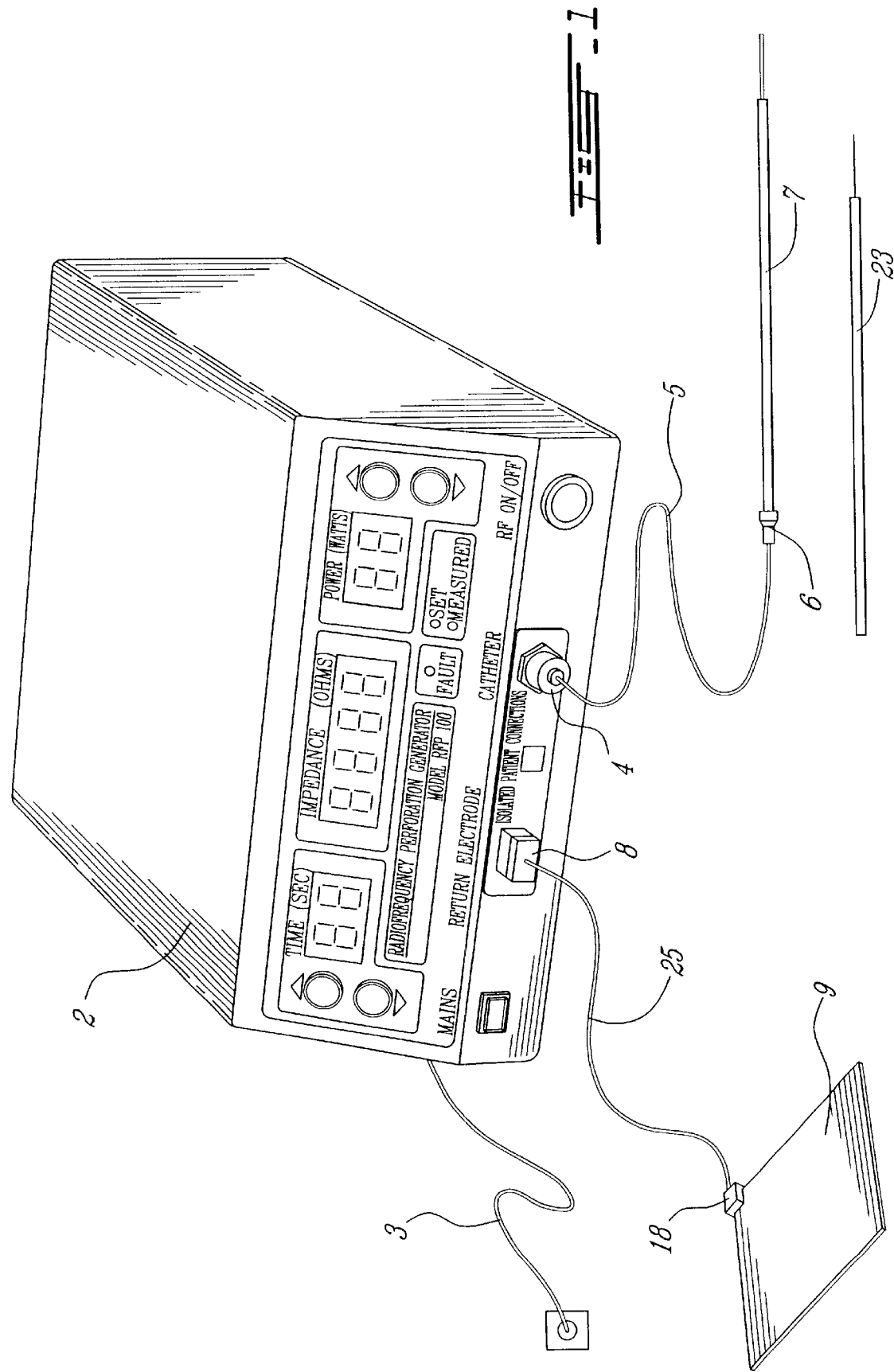
FIG. 1 is a perspective view of a preferred embodiment of the present invention.

In reference to the drawings in detail wherein like numerals indicate like elements throughout the several views, FIG. 1 is a perspective view of a preferred embodiment of the present invention. Guidewire system includes a radio frequency (RF) generator unit 2 which is powered through line cord 3 along which a ground wire runs (not shown) which plugs into a standard 110 volt AC grounded electrical socket (also not shown). The generator 2 like existing radio frequency generators is a voltage generating means connected to an electrically conductive guidewire to activate the uninsulated distal tip in a monopolar fashion. The voltage generating means or the generator includes a first and second terminals, where the first terminal is electrically connected to the guidewire, and the second terminal is electrically connected to a ground plate for attachment to a patient. The generator generates an alternating current voltage, which has a frequency in excess of 100 kilohertz which is in the radio frequency range.

Figure 10:
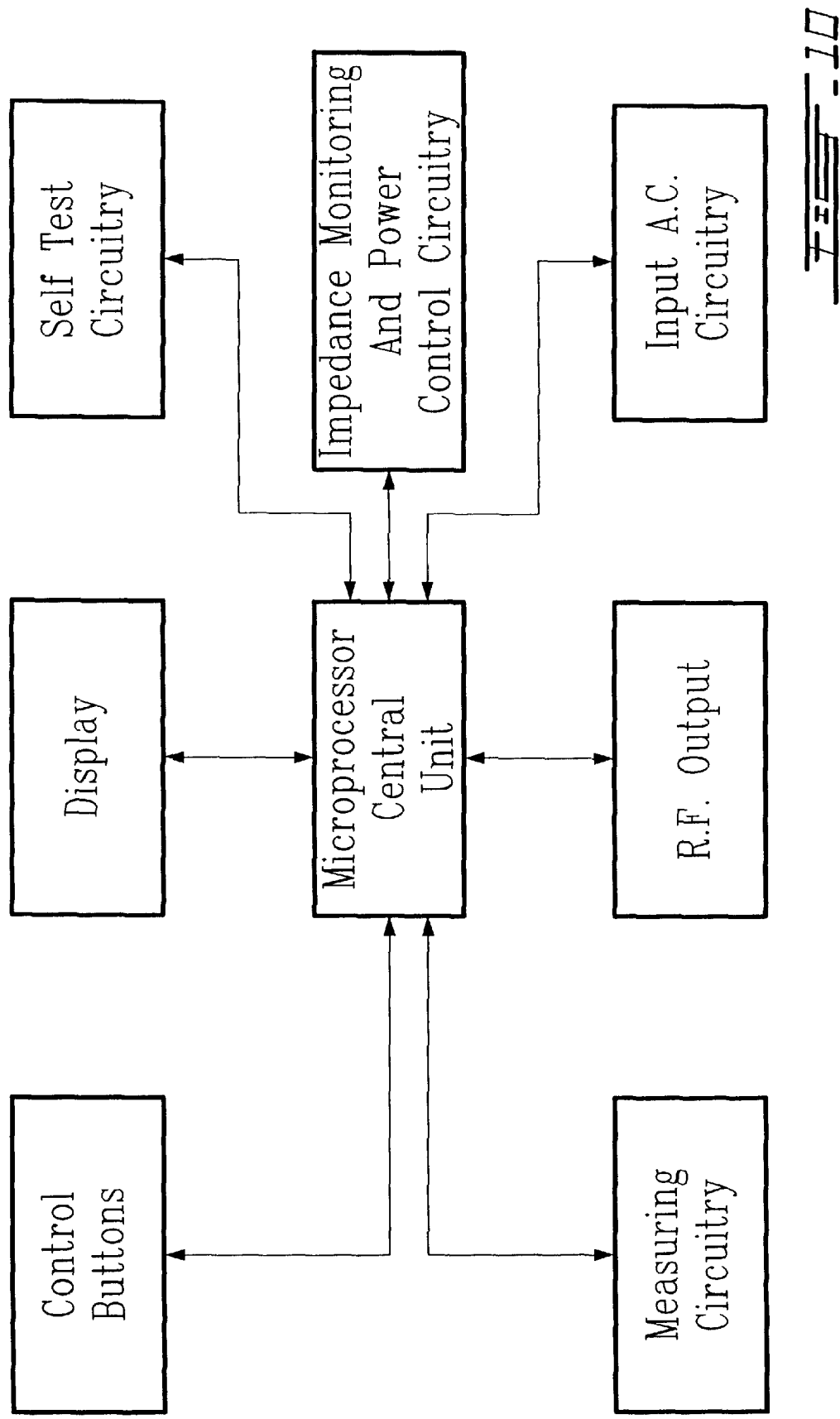
FIG. 10 is a block diagram of the building blocks of the generator.

The main components of the generator are shown in FIG. 10. The generator 2 is controlled by a microprocessor (not shown) which monitors all the electrical functions and regulates the generator. The microprocessor monitors both (true root mean square) RMS current and RMS voltage, and regulates the power output which is a function of both RMS current and RMS voltage. The microprocessor also monitors the impedance (which is calculated by dividing the instantaneous RMS voltage by the instantaneous RMS current), and will shut off the generator if the impedance measured is very low, below 100 ohms, or very high, greater than 6000 ohms. This exists to maintain patient safety.

Applicants have created an algorithm which will monitor impedance and compare impedance to a predetermined value to determine the end of the perforation process. When the RF generator is first turned on, and the guidewire is in contact with the tissue that needs to be perforated, an impedance value is measured and stored. This is the value that the microprocessor will compare against to determine the end of the perforation process. As the guidewire advances through the tissue, impedance will rise by about 20% and then level off, and this will be monitored and stored by the microprocessor. If impedance continues to rise rapidly, the microprocessor will shut off the generator, because it senses that there might be a coagulum build-up on the tip. During the impedance leveling off portion of the curve, variations of 5% either way will occur and these will be sensed by the microprocessor, but not acted on.

When the tip of the guidewire has perforated through the tissue, and is on the other side, impedance will drop by 20% or more, and this is the signal to the microprocessor to shut off the generator, but not acted on.

Figure 9:
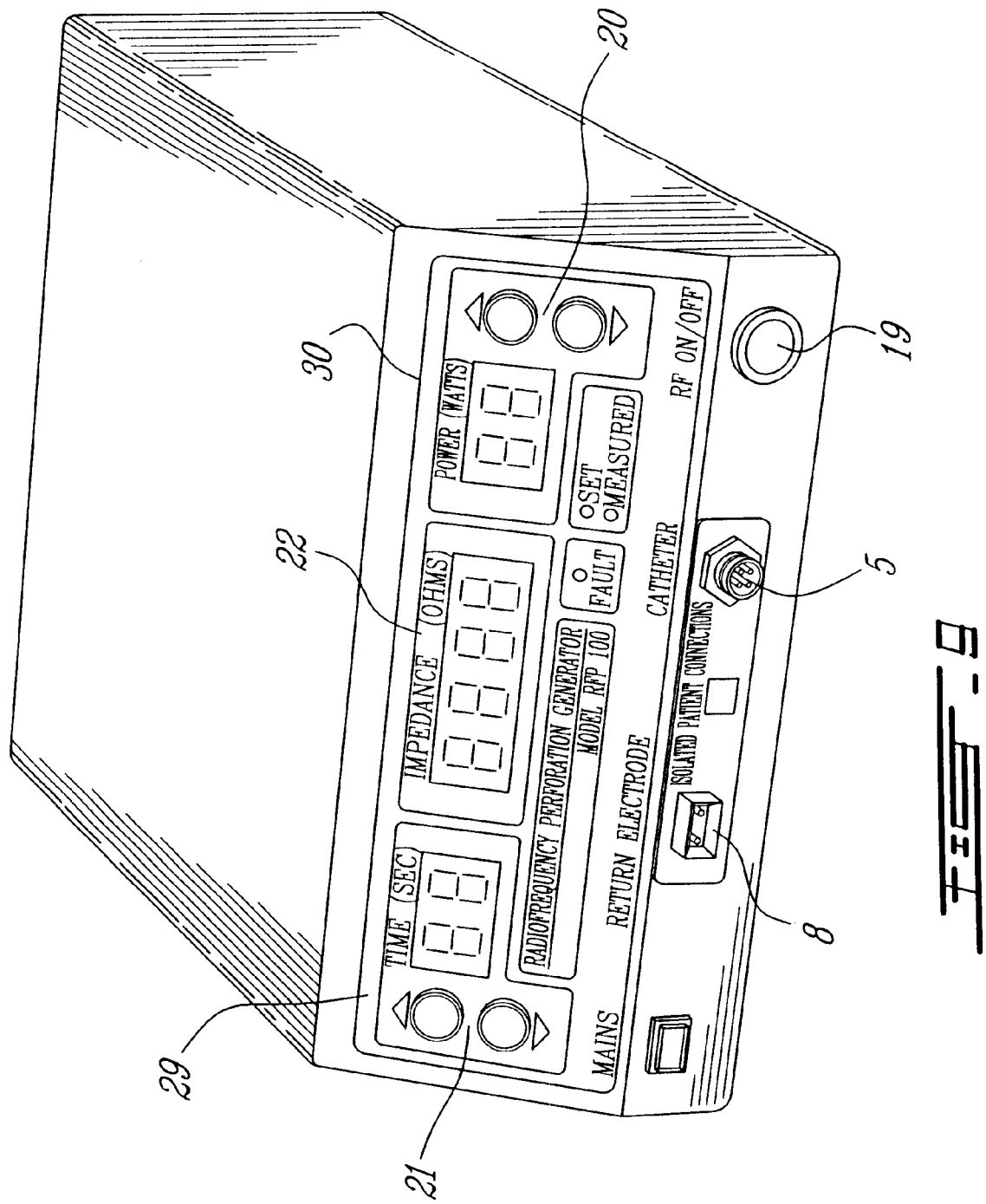
FIG. 9 is a frontal view of the RF generator.

FIG. 9 shows a frontal view of the RF generator unit 2. On the bottom right hand corner is located a push button on/off switch 19 which is used to power the unit. At the top right hand area is located the power setting switches and digital display 20 which allow the user to the set the power output in watts as required and furthermore allow the user to increment or decrement the power setting by steps of one watt as required. At the top left hand area is located the time setting switches and digital display 21 which allow the user to set the duration of the usage of the unit. The time setting controls, like the power switches, allow the user to increment or decrement the duration of time required. In the center of the console is a digital display 22 which allows the user to monitor the impedance in ohms.

With further reference to FIG. 1; at catheter connection terminal 4 of the RF generator unit 2 a connecting cable 5 is attached, which leads to a removable connection terminal 6 which is attached to guidewire 7. To the return electrode terminal 8 is attached a cable 25 which is coupled with a fixed connector 18 to a ground plate 9.

Removable connection terminal 6 fixedly engages and is electrically coupled to guidewire 7. The removable connection terminal 6 may be disconnected to allow further extension of guidewire 7 to another guidewire 23 with terminal 6 reconnected. In addition, removable connection terminal 6 may be disconnected to allow the advancement of a balloon catheter 24 or any another suitable surgical catheter (i.e. catheter lumen) over guidewire 7 or in place of guidewire 7. The removable connection terminal 6 may be slideably connected, locked-on, or connected in any other manner to guidewire 7.

Figure 2:
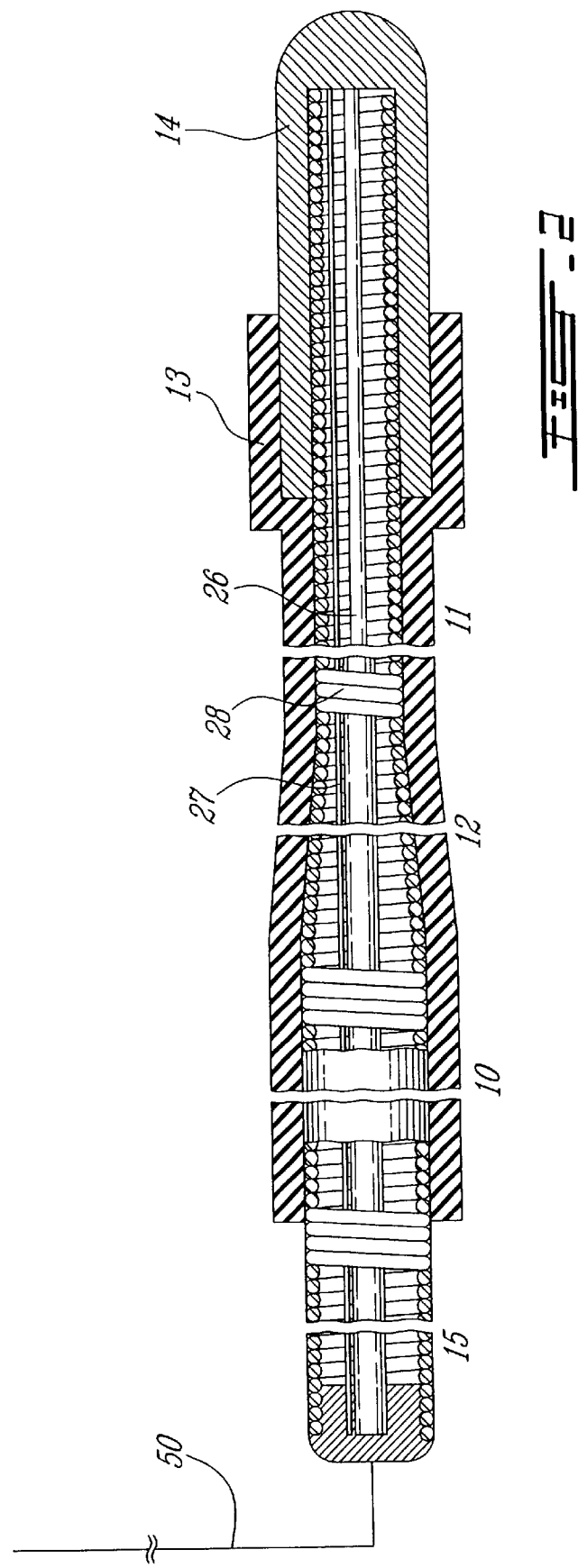
FIG. 2 is a cross-sectional view of the guidewire of the present invention.

Shown in FIG. 2 is the guidewire 7 of FIG. 1, which is a device having a distal tip portion 10, 11, 12 of non-uniform diameter, with the largest diameter region 10 being 0.05 cm in diameter, followed in the frontal direction by a dilator transition zone 12 of length 0.4 cm into the smallest diameter region 11, where the diameter is 0.035 cm. The guidewire 7 is constructed of stainless steel to provide high strength and corrosion resistance. The guidewire 7 consists of a tapered mandrel core 26, a safety wire 27, and a coil spring guide 28. To make the coil, one can begin with a long thin piece of wire, and coil it tightly, so that the spacing between each coil is uniform and approximately 0.03 cm. The preferred material is medical grade stainless steel. Alternatively, one can obtain a coil of the desired specifications which is preferably made of medical grade stainless steel. Guidewire 7 has sufficient insulation 13, which is 0.0125 cm thick, and extends from about 0.20 cm immediately behind the distal tip 14 to prevent RF energy distribution from any point other than tip 14 of guidewire 7. The insulation 13 extends to about 5 cm from the proximal end 15 of the guidewire 7, also called the handle 15 of the guidewire 7. The insulation 13 is preferably made of a suitable insulating material such as polytetrafluoroethylene (PTFE) or TEFLON™ due to its low coefficient of friction, good electrical insulating properties, high coefficient of resistance, high operating temperature, and high dielectric strength.

The dilator region 12 begins at about 3.3 cm immediately behind the distal tip 14, and extends for a length of 0.4 cm before translating into region 10. The function of the dilator 12 is to enlarge in a controlled manner the newly formed hole by distal tip 14.

The guidewire of FIG. 2 has varying stiffness due to its change in diameter. One of the factors that determine stiffness of a guidewire is the size of its outer diameter. The larger the diameter with all else constant, the stiffer the guidewire. Conversely, a guidewire with a smaller outer diameter, and all else constant will be less stiff. The dilator region, which can be of any length, tapers the overall diameter of the guidewire in FIG. 2 from a 0.05 cm diameter to a 0.035 cm diameter. If we divide the dilator region into 10 equal segments, each segment will have a different stiffness since no two segments will have the same outer diameter. Thus, the guidewire will have decreasing stiffness as we advance toward the tip through the dilator region. The tip region 11 thus exhibits a "floppy" characteristic.

The same properties can be provided in a guidewire that has a tapered core and uniform outer diameter. If one tapers the core gradually over a predefined length in the distal region, while maintaining the diameter of the outer coil constant, the guidewire will be more flexible as one advances toward the tip through the dilator region. This can be demonstrated by once again dividing the dilator region into 10 equal segments, and comparing the flexibility of each segment. No two segments will be equal in flexibility since the diameter of the core will be different in each segment. Thus the flexibility of the guidewire will increase as we approach the tip from the proximal end.

We can visualize the same reasoning for a guidewire that has both a tapered core and a tapered outer diameter. The distal portion of the guidewire will be of varying stiffness, and more flexible than the proximal portion and the body of the guidewire.

If we have a guidewire that is constructed out of a solid stainless steel wire only without any coil, if one tapers a predefined length in the distal region, such a guidewire will also have a varying stiffness profile.

As shown in FIGS. 6 and 7, balloon catheter 24 is a device that is constructed with a flexible wire core 33 on which a hypo-tube is welded and rounded to form a tip 14. The wire core 33 is of diameter 0.0125 cm and is surrounded by a flexible plastic tubing 32 of inner diameter 0.1 cm which is sealed to the wire core 33 in the distal region 2.25 cm behind the tip 14. The plastic tubing 32 goes through a transition region 34 before being completely sealed to the wire core 33. An insulation layer 13, 0.015 cm thick, covers the region from the distal end of the flexible plastic tubing 32, to the proximal end of the tip 14. The insulation 13 covers the exposed wire core 33, and does not allow any contact with the surrounding tissue. Approximately 4 cm behind the tip 14 a plastic balloon 31 of length 2 cm is glued on to the plastic tubing 32. The plastic balloon 31 has a diameter of 0.6 cm when maximally inflated. The balloon is preferably made out of polyethylene which can handle increased pressure, and maintain this pressure for longer periods of time. In addition, the balloon will not rupture easily, and is easily inflatable. This will reduce the inflation/deflation times considerably, reducing the procedure time. Furthermore, the polyethylene balloon can be made in extra thin wall, high strength, and also large diameter. Saline solution and contrasting dye is carried through the space in between the wire core 33 and the inner diameter of plastic tubing 32, and is allowed to escape into the plastic balloon 31 through holes 35.

Toward the proximal end of the balloon catheter 24 are certain devices which are shown in FIG. 8. Leak stopper 36 which is made out of plastic tubing and is 0.225 cm in outer diameter and 1.0 cm in length is glued onto plastic tubing 32, and is there to prevent any solution from escaping out of balloon adapter 37. Balloon adapter 37 begins approximately 0.4 cm behind the frontal end of leak stopper 36 and is of length 2.1 cm. The balloon adapter's 37 function is to allow the solution to flow from the pump (not shown) through pump adapter 41 and input tube 40 to the mouth opening 42 of plastic tubing 32. In addition, balloon adapter 37 allows core wire 33 to continue through leak stopper 38, (0.0225 cm outer diameter, length 4.8 cm) to removable connection terminal 6. This short exposed region of the guidewire is partially covered by insulation 13, from the proximal end of the leak stopper 38 to 5 cm short of the proximal end of guidewire 7. Furthermore, the balloon adapter 37 through its unique construction does not allow any solution to leak out of the contained system.

Figure 3:
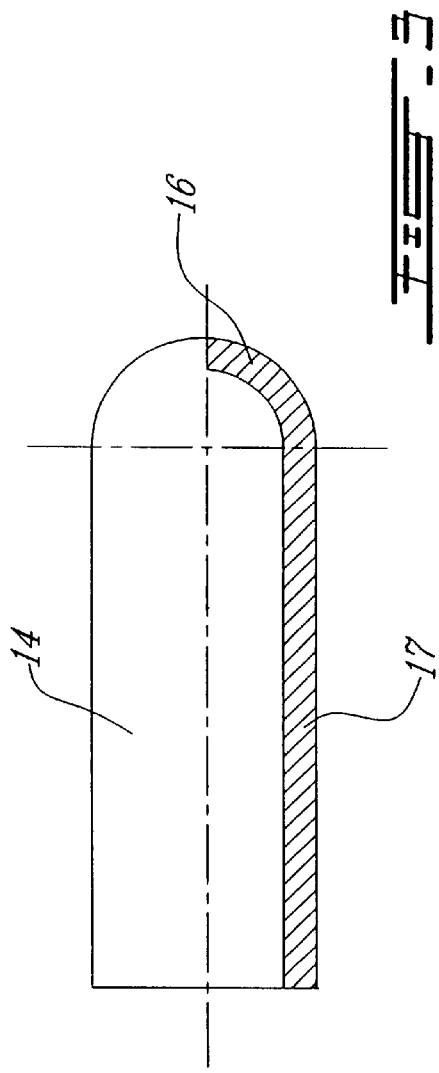
FIG. 3 is a cross-sectional view of the distal, hollow tip of the present invention.

The hollow distal tip 14 can be visualized as three regions as shown in FIG. 3. Semicircular region 16 of radius 0.010 cm and 2 rectangular regions 17 of length 0.24 cm with width of 0.010 cm. The tip 14 as shown facilitates creation, and then enlargement in a controlled manner, of a hole in the heart tissue, or any other tissue in the body as required. The distal tip 14 is designed in such a manner that it cannot perforate tissue with the sole application of manual force.

The hollow distal tip 14 is easy to form on guidewire 7 or balloon catheter 24 using arc welding techniques and solder. The tip electrode 14 is formed of Platinum with 20% Iridium. The tip 14 extends for 0.24 cm over the distal end of guidewire 7 and 0.04 cm of the tip 14 from its proximal end are covered by insulation 13.

Figure 4:
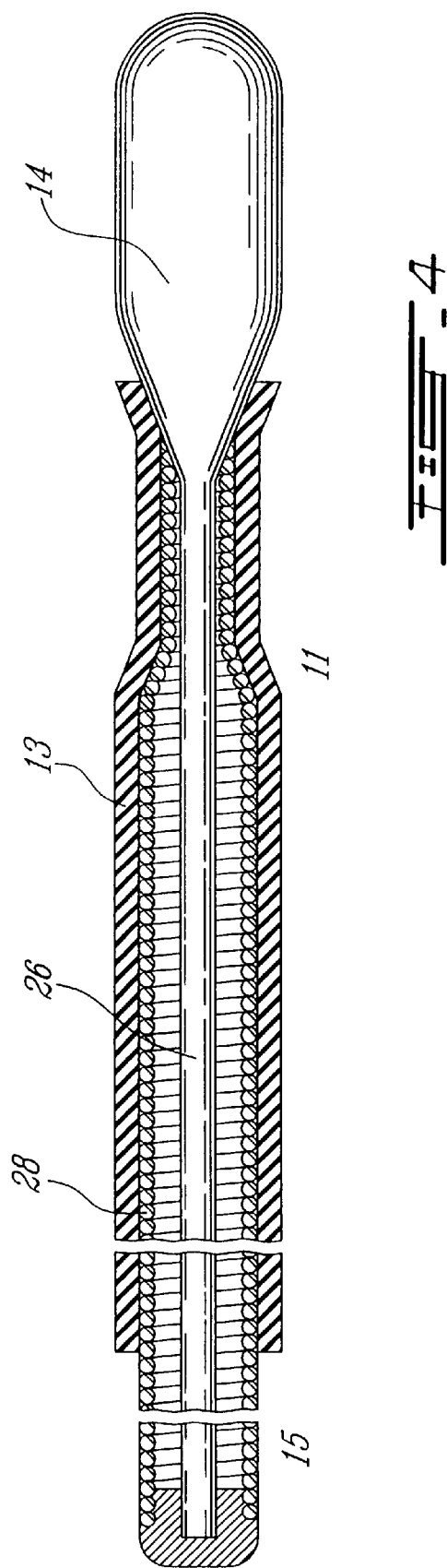
FIG. 4 is a cross-sectional view of the guidewire whose tip is an extension of its core.

As shown in FIG. 4, the tip can also be made such that it is an extension of the core body. We start of with a solid stainless steel 304 wire/rod, 165 cm in length, that has a diameter of 0.045 cm. Approximately 0.24 cm from one end, we begin grinding down the wire rapidly so that it has a diameter of 0.0125 cm after we have advanced 0.25 cm in length. We maintain this diameter for the entire length of the wire that is left, approximately 164.51 cm. The distal end that is 0.045 cm in diameter is then finely ground to round-off the end, giving it a smooth, rounded profile. A coil is then attached to the proximal end of the stainless steel wire with a weld, and then similarly welded to the wire approximately 0.35 cm from its distal end. Thus we have created a guidewire whose tip is an extension of the mandrel core. Guidewire 7 or balloon catheter 24 pass through an introduction catheter and are delivered to the electrosurgical site by use of standard angiographic techniques.

To use this invention, the ground plate 9 is attached to the patient using conductive jelly to ensure positive and dispersive electrical contact with the patient. At this point, there are two options:

A—using the guidewire 7 or

B—using the balloon catheter 24.

The choice is dependent on the particular circumstances and the procedure is similar.

The following describes option A. The introduction catheter and guidewire 7 are placed into the patient using standard angiographic techniques and are guided to the location of the tissue where the perforation is to be performed.

The user depresses the on/off switch 29 on the back of the unit, and the RF generator 2 is now in the POST mode of operation. Here it performs a self test of power generation, measurement and control circuitry. If all is satisfactory, the unit enters into READY mode, and if self-test fails, it enters into FAULT mode. In the READY mode, the power level 20 and the count-up timer 21 are settable. The impedance display 22 is blank, and the RF on/off switch 19 is not illuminated. Under these conditions, the audible tone is off. Now the user sets the power level 20 for 5 watts and the count-up timer 21 for 60 seconds. The RF generator 2 now is ready to energize electrically the tip 14 via the guidewire 7, removable connection terminal 6, connecting cable 5, and the connection terminal 4 of RF generator 2. The ON mode is initiated when the user depresses the on/off switch 19. Now the RF output is active and the on/off switch 19 is illuminated green. The timer display 21 counts up from 0 to the set time. RF output is terminated and the mode changes to the DONE (or FAULT) mode when the timer elapses, when the RF on/off switch 19 is pressed during the ON mode, or when an error is detected. Under these conditions, audible tone is on. Moderate pressure must be applied to the guidewire 7 in the distal direction to cause it to perforate a hole and advance therethrough, enlarging the hole in a controlled fashion using the dilator portion 12. It is important that constant longitudinal forward force be exerted during the delivery of the RF current to advance the tip 14 to create the adequate passageway required, and also to avoid localized dehydration which would cause coagulation on the guidewire tip 14.

In a preferred embodiment for intravascular use, once the RF generator 2 is activated, it will deliver the power level set consistently to the tip 14 in contact with the appropriate tissue over the full duration set. In the preferred embodiment, the energy delivered will cause the guidewire 7 to advance 2 millimeters per second in soft tissue. After the guidewire 7 has advanced the appropriate depth, the introduction catheter may be removed and the guidewire 7 is used to guide any of a variety of therapeutic devices (not shown) used to treat related disorders.

Once the set time is reached, the unit passes through the DONE mode as a transition from ON back to READY. DONE mode lasts for 5 seconds, then automatically changes to READY. The last measured power, impedance, and timer displays are held during the DONE mode.

Thermal effects of the passage of the guidewire 7 are minimal since the delivered power density falls off inversely as the fourth power of the distance from the tip 14 (i.e., power density is proportional to the square of the current density, and current density is inversely proportional to the square of the distance from the tip 14) and due also to the small size of the tip 14.

In a preferred embodiment, the output signal is a 500 kilohertz amplitude modulated, RF waveform with maximum output voltage of 224.0 V rms. into a resistive load of range 200 to 6000 ohms. The 500 kilohertz modulation reduces the overall power delivered to the tissue.

The following describes option B. The introduction catheter and the balloon catheter 24 are placed into the patient using standard angiographic techniques and are guided to the location of the tissue where the perforation is to be performed.

The user depresses the on/off switch 29 on the back of the unit, and the RF generator 2 is now in the POST mode of operation. Here it performs a self test of power generation, measurement and control circuitry. If all is satisfactory, the unit enters into READY mode, and if self-test fails, it enters into FAULT mode. In the READY mode, the power level 20 and the count-up timer 21 are settable. The impedance display 22 is blank, and the RF on/off switch 19 is not illuminated, and the audible tone is off. Now the user sets the power level 20 (e.g. for 5 watts) and the count-up timer 21 (e.g. for 60 seconds). The RF generator 2 now is ready to energize electrically the tip 14 via the balloon catheter 24, removable connection terminal 6, connecting cable 5, and the connection terminal 4 of RF generator 2. The ON mode is initiated when the user depresses the on/off switch 19. Now the RF output is active and the on/off switch 19 is illuminated green. The timer display 21 counts up from 0 to the set time. RF output is terminated and mode changes to DONE (or FAULT) mode when timer elapses, when RF on/off switch 19 is pressed during ON mode, or when an error is detected. Under these conditions, audible tone is on. Moderate pressure must be applied to the balloon catheter 24 in the distal direction to cause it to perforate a hole, and advance through the hole, enlarging the hole in a controlled fashion by expanding the balloon 31. It is important that constant longitudinal forward force be exerted during the delivery of the RF current to advance the tip 14 to create the adequate passageway required, and also to avoid localized dehydration which would cause coagulation on the balloon catheter tip 14.

In a preferred embodiment for intravascular use, once the RF generator 2 is activated, it will deliver the power it is set for consistently to the tip 14 in contact with the appropriate tissue over the full E duration it is set for. The energy delivered will cause the balloon catheter 24 to advance at a preferred rate of 2 millimeters per second in soft tissue. After the balloon catheter 24 has advanced the appropriate depth, the introduction catheter may be removed and the balloon catheter 24 may be used to guide any of a variety of therapeutic devices (not shown) used to treat related disorders.

Once the set time is reached, the unit passes through the DONE mode as a transition from ON back to READY. The DONE mode lasts for 5 seconds (or any suitable period), and then automatically changes to READY. The last measured power, impedance, and timer displays are held during the DONE mode.

Thermal effects of the passage of the balloon catheter 24 are minimal since the delivered power density falls off inversely as the fourth power of the distance from the tip 14 (i.e., power density is proportional to the square of the current density, and current density is inversely proportional to the square of the distance from the tip 14) and due also to the small size of the tip 14.

In a preferred embodiment, the output signal is a 500 kilohertz amplitude modulated, RF waveform with maximum output voltage of 224.0 V rms. into a resistive load of range 200 to 6000 ohms. The 500 kilohertz modulation reduces the overall power delivered to the tissue.

Thus, the several aforementioned objects and advantages are most effectively attained. Although preferred embodiments of the invention have been disclosed and described in detail herein, it should be understood that this invention is in no sense limited thereby and its scope is to be determined by the appended claims.

We claim:

1. A method for creating a hole in body tissue to be perforated and then enlarging said hole, using an elongated instrument, said instrument having an electrically insulated electrical conductor, an electrically conductive exposed tip for creating a perforation when Radio Frequency (RF) current is applied and for preventing the creation of a perforation when RF current is not applied and a body of said instrument near said tip having a larger diameter than said tip, comprising the steps of:

inserting said instrument in a body cavity and guiding said instrument to a location where said body tissue to be perforated is;

advancing said instrument to contact a wall of said body tissue to be perforated without applying RF current;

emitting RF current at said tip to perforate said body tissue to be perforated;

advancing said instrument into said perforation to pass through said tissue;

turning off said RF current and expanding said hole by advancing said instrument through the perforation.

2. The method as claimed in claim 1, wherein a flexibility of said tip is such that, when guided against an occlusion, said tip is likely, in the absence of RF current, to bend and not create a perforation.

3. The method as claimed in claim 1, further comprising connecting a surgical device to a proximal end of said instrument.

4. The method as claimed in claim 3, wherein said surgical device is an adapter for connection to a source of RF current and said method further comprises providing RF current to said tip by connecting said adapter to said source of RF current and enabling said source of RF current.

5. The method as claimed in claim 1, further comprising measuring an impedance of said tip;

detecting a change in said impedance; and providing an indication of the position of said tip in relation to said body tissue to be perforated, said indication being provided in response to said measurement of impedance of said tip.

6. The method as claimed in claim 1, further comprising, after said expanding, delivering fluid to an inflatable balloon located circumferentially on said elongated instrument;

further expanding said hole by inflating said inflatable balloon using said fluid.

7. The method as claimed in claim 6, further comprising providing a catheter in communication with said balloon and said elongated instrument for delivery of fluid to said balloon for its inflation.

8. A method for creating a hole in body tissue to be perforated and then enlarging said hole comprising the steps of:

providing an elongated instrument having a proximal end, a distal end and an elongated portion between said proximal end and said distal end;

a tip portion including an electrically conductive exposed tip for creating a perforation when Radio Frequency (RF) current is applied and for preventing the creation of a perforation when RF current is not applied;

an electrically insulated electrical conductor for passing electric current from said proximal end of said instrument to said tip; and a dilator region between said tip and said elongated portion at said distal end, for expanding said hole, and having a tapered profile, inserting said instrument in a body cavity and guiding said instrument to a location where said body tissue to be perforated is;

advancing said instrument to contact a wall of said body tissue to be perforated without applying RF current;

emitting RF current at said tip to perforate said body tissue to be perforated;

advancing said instrument into said perforation to pass through said tissue;

turning off said RF current and expanding said hole by advancing said instrument through the perforation.

9. The method as claimed in claim 8, wherein a flexibility of said tip is such that, when guided against an occlusion, said tip is likely, in the absence of RF current, to bend and not create a perforation.

10. The method as claimed in claim 8, further comprising connecting a surgical device to a proximal end of said instrument.

11. The method as claimed in claim 10, wherein said surgical device is an adapter for connection to a source of RF current and said method further comprises providing RF current to said tip by connecting said adapter to said source of RF current and enabling said source of RF current.

12. The method as claimed in claim 8, further comprising measuring an impedance of said tip;

detecting a change in said impedance; and providing an indication of the position of said tip in relation to said body tissue to be perforated, said indication being provided in response to said measurement of impedance of said tip.

13. The method as claimed in claim 8, further comprising, after said expanding, delivering fluid to an inflatable balloon located circumferentially on said elongated instrument;

further expanding said hole by inflating said inflatable balloon using said fluid.

14. The method as claimed in claim 13, further comprising:

providing a catheter in communication with said balloon and said elongated instrument for delivery of fluid to said balloon for its inflation.

\* \* \* \* \*